United States Patent [19]
Klatz et al.

[11] Patent Number: 5,149,321
[45] Date of Patent: Sep. 22, 1992

[54] BRAIN RESUSCITATION DEVICE AND METHOD FOR PERFORMING THE SAME

[76] Inventors: Ronald M. Klatz, 1510 Montana St.; Robert M. Goldman, 2434 N. Greenview, both of Chicago, Ill. 60614

[21] Appl. No.: 595,387

[22] Filed: Oct. 10, 1990

[51] Int. Cl.$^5$ .......................................... A61M 21/00
[52] U.S. Cl. .................................................. 604/52
[58] Field of Search ....................... 604/24, 26, 29, 49, 604/52

[56] References Cited

U.S. PATENT DOCUMENTS

| | | | |
|---|---|---|---|
| 4,378,797 | 4/1983 | Osterholm | 604/26 X |
| 4,393,863 | 7/1983 | Osterholm | 604/52 X |
| 4,445,500 | 5/1984 | Osterholm | 604/52 X |
| 4,657,532 | 4/1987 | Osterholm | 604/24 |

OTHER PUBLICATIONS

Elrifai et al., "The Use of Blood Substitutes for Whole Body Perfusion in Ultra-Profound Hypothermic Cardiac Arrest", *Annals of Clinical and Laboratory Science*, vol. 20, No. 4, p. 192 (Jul.-Aug. 1990).
"Nutritional Aspects of Ambulatory Care", *American Family Physicians*, vol. 42, No. 3, pp. 557-558 (Sep. 1990).
White, "Cerebral Ischemic Injury", *Emergency Medicine, A Comprehensive Study Guide*, pp. 9-10 (1988).
Asbury et al., "Diseases of the Central Nervous System", pp. 1071, 1083 (1986).
Nordstrom et al., "Cerebral Blood Flow, Vascoreactivity, and Oxygen Consumption During Barbiturate Therapy in Severe Traumatic Brain Lesions", *J. Neurosurgery*, 68:424-431 (1988).
"At Surgery's Frontier: Suspended Animation", *New York Times*, C1, C12 (Nov. 13, 1990).
"A Randomized Clinical Study of Thiopental Loading in Comatose Survivors of Cardiac Arrest", *N. Engl. J. Med.*, 314: 397-403 (1986).
Rogers et al., "Current Concepts in Brain Resuscitation", *J. American Medical Assn.*, vol. 261, No. 21, pp. 3143-3147 (1989).
Donegan et al., "Cerebralvascular Hypoxic and Autoregulatory Responses During Reduced Brain Metabolism", *Am. J. Physiol.*, vol. 249, H421-429 (1985).
Lee et al., "Regional Cerebral Blood Flow in Normal Blood Circulated and Perfluorocarbon Transfused Rats", *Adv. Exp. Med. Biol.*, vol. 200, pp. 59-65 (1986).
Spiess et al., "Protection from Cerebral Air Emboli with Perfluorocarbons in Rabbits", *Stroke*, vol. 17, No. 6, pp. 1146-1149 (1986).
Simpson et al., "Free Radicals and Myocardial Ischemia and Reperfusion Injury", *J. Lab. Clin. Med.*, pp. 13-30 (Jul. 1987).
Hiraga et al., "Increase in Brain Tumor and Cerebral Blood Flow by Blood-Perfluorochemical Emulsion (Fluo-sol-DA) Exchange", *Cancer Research*, vol. 47, No. 12, pp. 3296-3302 (1987).
Clark et al., "Polarographic Cerebral Oxygen Availability, Fluorocarbon Blood Levels and Efficacy of
(List continued on next page.)

*Primary Examiner*—William H. Grieb
*Attorney, Agent, or Firm*—Robins, Kaplan, Miller & Ciresi

[57] ABSTRACT

This invention discloses a method for resuscitating the brain as a result of ischemic and anoxic injuries whereby the patient survives neurologically intact. The method includes the steps of catheterizing the patient's circulatory system and introducing a temperature controlled solution to cool the brain to a coma and a state of hypothermic shock, further driving the brain into a submetabolic coma, oxygenating the brain and inhibiting free radical damage, and continuing additional efforts at life support. The temperature controlled brain resuscitation solution includes barbituates, perfluorocarbons, antioxidants, brain and neurologic tissue damage reversing and protecting agents, carrier vehicles, diluents, nutrients, and anti-coagulating agents. A device which performs this method is also disclosed. This device includes a fluid reservoir, an oxygen tank, a heat exchanger and removable catheter lines.

33 Claims, 2 Drawing Sheets

OTHER PUBLICATIONS

Oxygen Transport by Emulsions", *Biomaterials*, 16(1-3), pp. 375-393 (1988).

Clark et al., "The Nature of Fluorocarbons Enhanced Cerebral Oxygen Transport", *Adv. Exp. Med. Biol.*, vol. 248, pp. 341-355 (1989).

"Easier Breathing in RDS", *Medical Tribune*, Jan. 11, 1990.

White, "Cerebral Ischemic Injury", *Resuscitative Problems and Techniques*.

"'90s Could See Brain Injury Reversal", *American Medical News*, p. 66 (Nov. 17, 1989).

"Cooling Brain May Limit Stroke Damage", *American Medical News*, p. 66 (Nov. 17, 1989).

"Drug May Preserve Heart Tissue After Attack", *New York Times*, p. 3, Sep. 5, 1989.

"Nutritional Aspects of Ambulatory Care"–Adapted from An Internal Med. 107: 528 (1987).

"Radical Therapy", *Scientific American*, Sep. 1987.

Pluta, "Resuscitation of the Rabbit Brain After Acute Complete Ischemia Lasting up to One Hour: Pathophysiological and Pathomorphological Observations", *Resuscitation*, 15: 267-287 (1987).

Asbury et al., *Diseases of the Central Nervous System*, p. 1071.

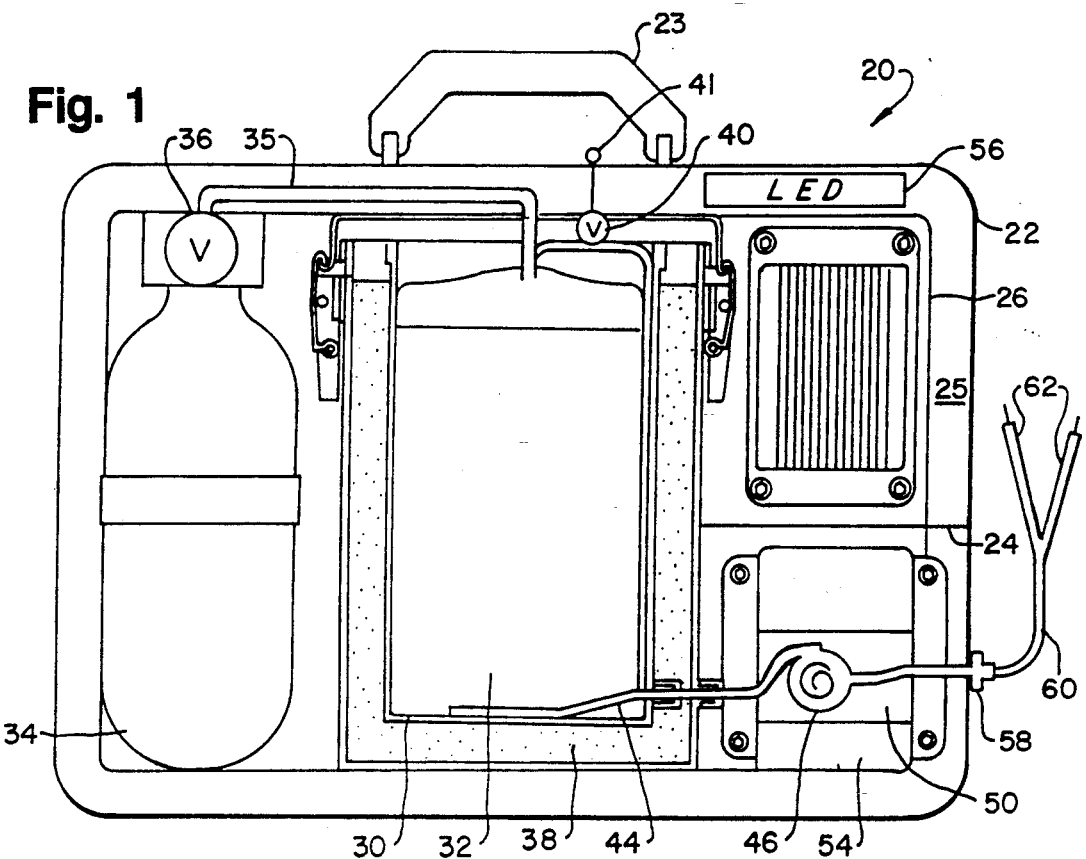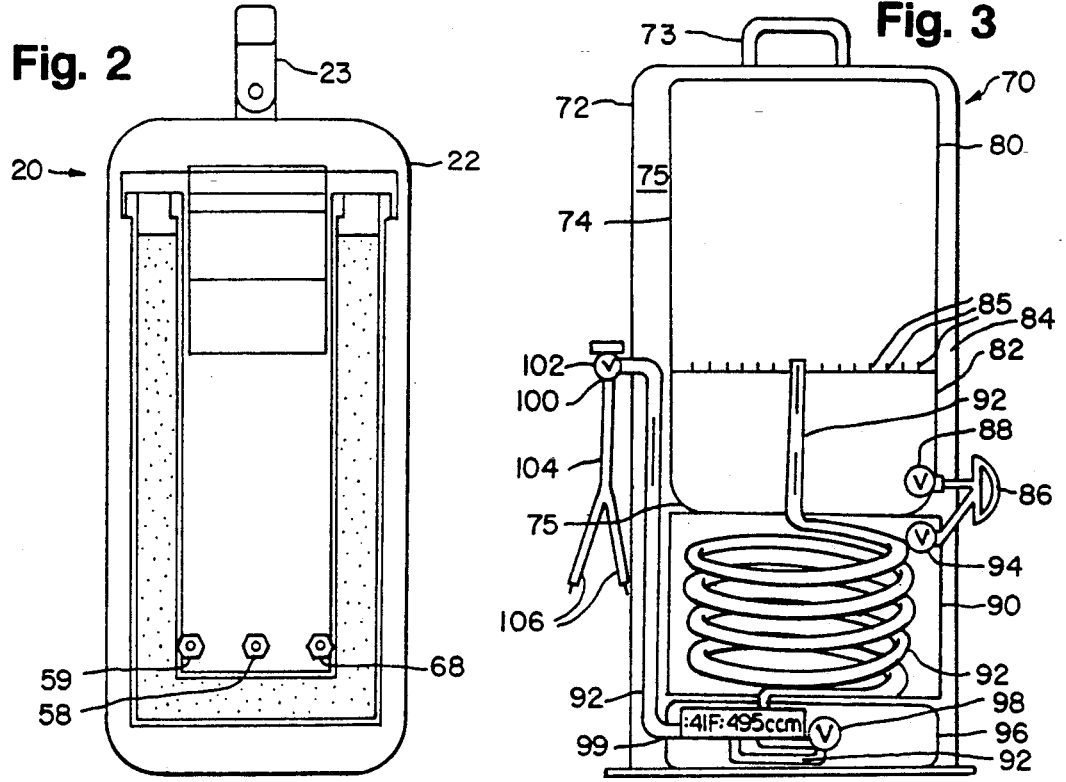

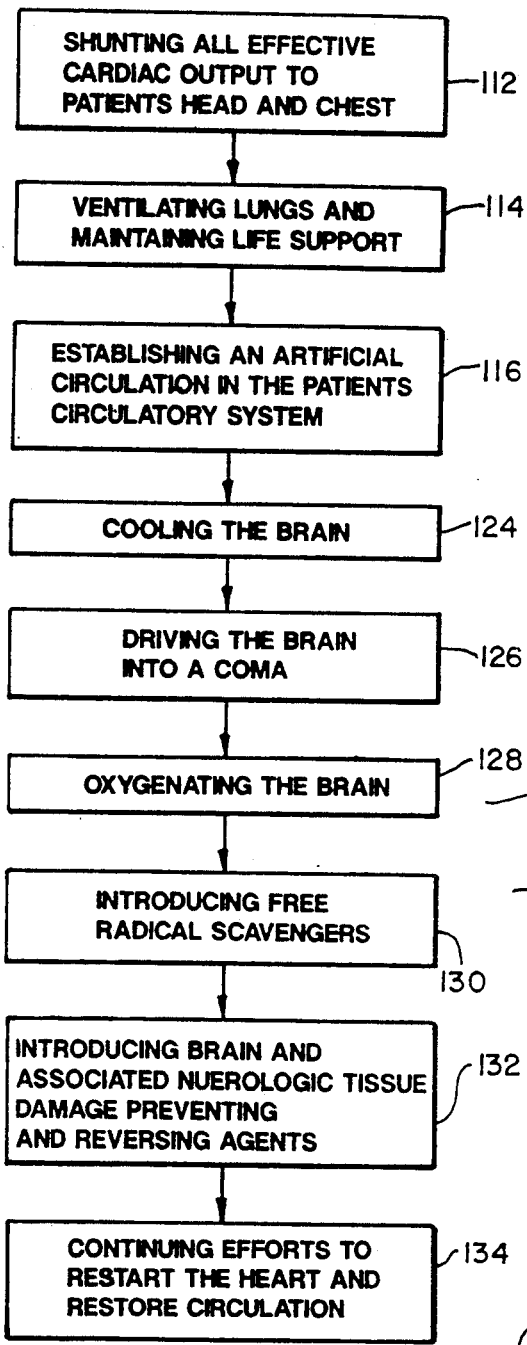
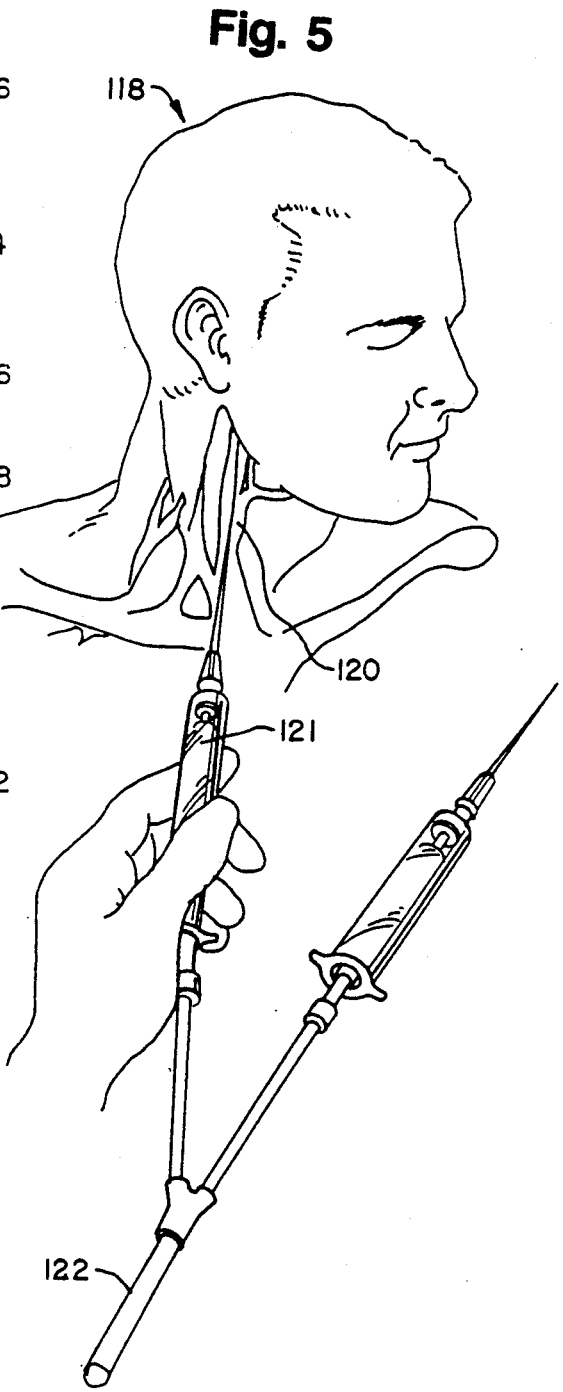
Fig. 5
Fig. 4

BRAIN RESUSCITATION DEVICE AND METHOD FOR PERFORMING THE SAME

FIELD OF THE INVENTION

The present invention relates generally to treating ischemic and anoxic brain injuries associated with cardiac arrest. More particularly, the present invention provides an apparatus and method for resuscitation of the brain and maintenance of viability during trauma or other periods of decreased blood flow, allowing the health professional extra time to restore blood circulation. With the present invention, the brain and associated neurologic tissues remain intact, throughout attempts to restart the victim's heart and restore circulation, allowing the victim increased chances of survival with less chance of permanent brain damage.

BRIEF DESCRIPTION OF THE PRIOR ART

During cardiac arrest, the heart ceases to pump blood. Subsequently, there is no circulation, and the brain fails to receive freshly oxygenated blood. Without a steady supply of oxygenated blood, the brain will cease to function.

Current resuscitation techniques for cardiac arrest have been directed almost exclusively towards the heart. However, even with methods such as cardiopulmonary resuscitation (CPR), patient survival rates are low. In hospitals and clinics with advanced CPR and life support systems, the survival rate is normally around 14%. Outside of hospital settings, the survival rate is about 5%.

Among cardiac arrest victims overall, less than 10% survive neurologically intact and without significant brain damage. The other approximately 90% either die or sustain some neurologic injury from ischemia, (i.e., lack of blood flow to the brain), or anoxia (i.e., lack of oxygen to the brain). Such frequency of neurologic injury occurs because after cardiac arrest, basic cardiopulmonary resuscitation and advanced life support techniques, such as CPR, closed heart cardiac chest massage, and electroshock treatments, typically require fifteen to twenty minutes to regain circulation from a failed heart. Reversible neurologic damage begins as early as four minutes and irreversible neurologic damage begins as early as six minutes after circulation stops. To combat this potential neurologic injury, initial resuscitation efforts need to be directed toward reviving the brain in addition to resuscitating the heart.

As indicated above, anoxic and ischemic brain injuries from cardiac arrest result in damage to the brain and associated neurologic tissues after about four minutes. In contrast, the heart can survive intact up to four hours after cardiac arrest. The short viability of brain tissue upon deprivated oxygenated blood is a result of the requirement of high amounts of nutrients for tissue maintenance. Brain tissue uses almost all of the nutrients supplied by the circulating blood for maintenance and has very little remaining for storage. Absent blood flow to the brain, the small amount of stored nutrients is rapidly exhausted. Once exhausted, brain oxygen content rapidly depletes. This oxygen depletion is traumatic and causes a series of reactions in the oxygen starved brain tissue cells. These reactions produce free radical ions, primarily consisting of the superoxide radical $O_2^-$. These free radicals complex with proteins in the brain and associated neurologic tissues, altering respiration, energy transfer and other vital cellular functions, and irreversibly damaging these tissues.

Prior efforts at resuscitating the brain have involved highly invasive treatments, intruding physically into the brain itself. Such invasive techniques are described in U.S. Pat. Nos. 4,378,797 and 4,445,500 issued to Osterholm. These patents describe a stroke treatment method which is a direct physical intrusion into the brain itself. In this method, an opening is drilled directly through the skull through the brain into the pons or brain ventricles. These areas are then directly cannulated and flooded with room temperature oxygenated perflurocarbons. These entering perflurocarbons mix with cerebral spinal fluid, whereby they are carried throughout the brain and associated neurologic tissues through channels within the central nervous system, sometimes referred to as the "third circulation." Excess fluid is drained through an opening invasively placed in the cisterna magna of the brain.

This stroke treatment method has several drawbacks. This method must be performed in a surgical environment by a skilled surgical team. It can not be done by a single person with basic medical training. It can not be done in the field or other emergency type settings. The device used in performing this stroke treatment is not portable. Additionally, since this procedure is invasive (drilling directly into the brain), there is a high risk of mechanical damage to the brain and associated neurologic tissues. Finally, the treatment fluid used contains essentially perflurocarbons. It lacks any agents needed to inhibit free radical damage.

It is therefore an object of this invention to non-invasively treat ischematic and anoxic brain injuries immediately upon cardiac arrest whereby resuscitation efforts are applied in time for a patient to survive neurologically intact. By directing resuscitating efforts to immediately treating the brain, the present invention allows medical personnel substantial additional time (beyond the critical four minute window) to regain the failed heart's circulation without the patient suffering neurologic damage.

It is also an object of the invention to provide a method of treating ischemic and anoxic brain injuries suffered upon cardiac arrest so as to inhibit free radical chemical species from complexing with proteins in the brain and neurologic tissue to avoid permanent irreversible damage.

It is another object of the invention to resuscitate the brain by establishing a non-invasive, artificial circulation of synthetically oxygenated blood to the brain.

It is yet another object of the invention to prevent and reverse potential damage to the brain and associated neurologic tissue suffered as a result of ischemic injury due to cardiac arrest, major trauma, suffocation, drowning, electrocution, blood loss and toxic poisoning from substances including carbonmonoxide and cyanide.

It is a further object of the invention to provide a device for treating the aforementioned injuries, which is suited for field as well as clinical use and that can be operated by a single person with minimal medical training and experience.

It is still another object of the invention to provide a solution capable of inhibiting free radical ions from complexing with proteins in brain and associated neurologic tissue, and capable of protecting these tissues and reversing injuries to these tissues, thereby expanding the brain's critical four minute viability window.

SUMMARY OF THE INVENTION

The present invention focuses on initial resuscitation efforts toward resuscitating the brain due to its short viability, rather than the heart. The invention includes a non-invasive method which reverses and inhibits neurologic damage, and resulting ischemic and anoxic injury upon cardiac arrest. The method includes establishing an artificial circulation by catheterizing the circulatory system in both external carotid arteries, to deliver essential treatment components in a synthetic brain resuscitation solution to the brain. Once catheterized, the brain is driven into a submetabolic coma as barbiturates are introduced through the catheter. This coma lowers the brain's metabolism and decreases free radical production, while keeping its tissues viable. The brain is oxygenated by introducing temperature controlled perfluorocarbons, which are super-saturated with oxygen. These perfluorocarbons act as a blood substitute and transport oxygen in a manner similar to hemoglobin. Free radical damage is inhibited by introducing antioxidants, free radical scavengers. The antioxidants complex with the ionic $O_2^-$ and prevent the ions from complexing with proteins in brain tissue, which is a cause of irreversible damage. Protecting and reversing neurologic damage is accomplished by introducing Lazeroids, an experimental drug class now being developed by the Upjohn Pharmaceutical Company of Kalamazoo, Mich.

All of the above-mentioned compositions are included in a single brain resuscitation solution. This brain resuscitation solution is delivered to the brain in a chilled condition. The fluid is chilled by cooling it to a temperature sufficiently low to hypothermically shock the brain. At this point, the brain's metabolism is slowed and free radical production decreases. The brain is additionally cooled externally with natural or synthetic ice packs around the patient's head.

Once the procedure is complete, continuing efforts are then made to resuscitate the heart and restore the circulation. This can be achieved by drug administration, CPR (manual and mechanical), chest compression, and the like.

The present invention includes a device for delivering the aforementioned brain resuscitation solution. The device can be adapted for clinical or field use. This device includes a reservoir for holding the brain resuscitation solution which communicates with an oxygen tank and a heat exchanger. Upon activation, the oxygen is released into the reservoir, oxygenating the brain resuscitation solution. The oxygenated solution is then pumped from the reservoir to the heat exchanger, where it is cooled. The cooled solution is then introduced to the patient's circulatory system through the catheterized carotid arteries or other blood vessels and directed toward the brain.

BRIEF DESCRIPTION OF THE DRAWINGS

For a more complete understanding of the invention reference should be made to the drawings wherein:

FIG. 1 is a front view of the portable brain resuscitation device of the invention illustrating the internal components;

FIG. 2 is a side view of the portable brain resuscitation device of FIG. 1;

FIG. 3 is a front view of a second embodiment of portable device shown in FIG. 2;

FIG. 4 is a flow chart of the method of the present invention; and

FIG. 5 is a front view of the patient being catheterized.

DETAILED DESCRIPTION OF THE DRAWINGS

Referring to FIGS. 1 and 2, the brain resuscitation device 20 of this embodiment of the invention is semiautomatic. It includes an outer casing 22 with a handle 23 and a window 24. The window 24 is located within a first side 25 which has a greater width than length. The casing 22 includes an inner chamber 26. This inner chamber 26 contains components which include a reservoir 30, an oxygen tank 34, a heat exchanger 38, a pump 46, a logic control unit 50, and a power source 54.

The reservoir 30 holds the brain resuscitation solution. This solution of this invention is a fluid mixture of various components and is packaged in premixed, premeasured cannisters, for a single immediate use. These canisters can be replenished (refilled) and exchanged for continued life support. The specific components are discussed below in accordance with the method of the invention. Preferably, this reservoir 30 is adapted to hold three liters of fluid contained within replacable canisters 32. The preferred canisters are clear plastic bags, such that fluid depletion in the reservoir 30 can be viewed through the window 24. However, these canisters can be rigid containers, made of opaque material.

An oxygen tank 34, adjustable to various pressures, communicates with reservoir 30 through a first conduit 35. Oxygen tank 34 is sealed by a valve 36, which is opened once the device 20 is activated. Tank 34 is preferably a cylinder ten inches tall by four inches in diameter, containing oxygen pressurized to at least 17 psig.

A heat exchanger 38 capable of controlling the fluid's temperature, surrounds reservoir 30. Preferably the heat exchanger cools by undergoing an internal endothermic reaction, once a charging valve 40 is opened when a charging handle 41 on the device 20 is activated. The exchanger contains Ammonium Nitrate and water, which are initially separate. Upon activation, these chemicals contact each other, reacting endothermically, causing the heat exchanger to cool. Additionally, the heat exchanger's cooling can be accomplished by Carbondioxide (dry ice), freon or a mechanical cooling device.

A second conduit 44 extends from the reservoir 30 and communicates with a valve controlled pump 46 in communication with a logic control unit 50. The pump 46 and the logic control 50 unit are both powered by an energy source 54. However, the device is suitable for an electric adapter. A battery pack is the preferred energy source 54. The logic control unit 50 includes (not shown) an oxygen pressure sensor, a fluid mass flow sensor, a fluid pressure indicator and regulator, a fluid temperature indicator and regulator, a fluid temperature indicator with feedback to a mass sensor, and a timing device for estimating the time the fluid in the reservoir 30 will be depleted at a given mass flow. Measurements from logic control unit 50 are displayed on an LED digital display 56. Digital display 56 preferably shows the temperature and flow rate of the brain resuscitation solution.

The second conduit 44 extends through the pump 46 and logic control unit 50 and terminates in a side opening 58 on the device 20. Preferably, this side opening 58 is on the side 66 adjacent to the longitudinal side 25.

Side opening 58 is capable of attaching to catheter lines 60 to permit brain resuscitation solution to enter the patient's circulatory system, through catheters 62 placed into a single, but preferably both, external or internal carotid arteries.

With respect to catheters 62, one way balloon tipped catheters are preferred. The balloons generally inflate upon activation to block potential reverse blood and brain resuscitation fluid flow toward the heart. Additionally, it is preferred that this adjacent side 66 also contain openings for venting excess oxygen 68 and for oxygen intake 69. This oxygen intake can be from the atmosphere or from adjunct oxygen sources.

Upon activating the brain resuscitation device, the oxygen tank valve 36 opens and pressurized oxygen is released from the oxygen tank 34 into contact with the brain resuscitation fluid, thereby oxygenating it. The heat exchanger 38 is activated by releasing the charging valve 40. Once activated, the oxygenated solution in the reservoir 30 is cooled. This cooled solution moves through a second conduit 44, drawn by sufficient pressure from the oxygen tank 34 into a logic control unit 50, powered by an energy source 54, such as a battery pack. A pump 46, within this logic control unit 50 further moves the chilled oxygenated solution through this second conduit. Solution then enters a catheter line 60, attached to an opening 58 in device 20 whereby it is delivered to the brain through the catheters 62.

The preferred embodiment of the brain resuscitation device 20 is relatively small. It is portable, suitcase-like in appearance, and suitable for field use, such as in ambulances, battlefields, athletic fields, aircraft, marine vehicles, spacecraft, emergency treatment facilities, and the like. It is lightweight and can be carried directly to the patient. In one example of the device the outer casing measures twenty inches by eighteen inches by fifteen inches and weighs approximately thirty pounds.

FIG. 3 is a second embodiment of the brain resuscitation device 70. This embodiment is mechanical. It is manually activated and is fully operative under pneumatic power generated by pressurized oxygen. Device 70 includes an outer casing 72 with a handle 73 and preferably a window 74, located in a first side 75 having a greater length than width. The outer casing 72 includes an inner chamber 76. This inner chamber 76 contains components which include a reservoir 80, an oxygen tank 82, a heat exchanger 90, and a logic control unit 96.

The reservoir 80 holds the brain resuscitation solution of the invention. The brain resuscitation solution is a mixture of various components and is packaged in premixed, premeasured cannisters, for a single immediate use. These cannisters can be replenished (refilled) and exchanged for continued life support. The specific components of the brain resuscitation solution are discussed below in accordance with the method of the invention. Preferably, reservoir 80 is adapted to hold four to ten liters of solution contained within replacable canisters 84. The preferred cannisters are clear plastic bags through which the fluid depletion in the reservoir 80 can be viewed through the window 74.

Reservoir 80 communicates with an oxygen tank 82 through channels 85, which open when a charging handle 86 is pulled. Oxygen tank 82 is adjustable to various pressures and is sealed by a valve 88 on the charging handle 86. The oxygen is pressurized to at least 17 psig.

Reservoir 80 also communicates with a heat exchanger 90, capable of controlling the solution's temperature, through a conduit 92. Similar to that of the first embodiment, the preferred heat exchanger cools by undergoing an internal endothermic reaction, as explained with the first embodiment above. Heat exchanger 90 communicates with the charging handle through a valve 94, which when activated by pulling, initiates cooling.

Conduit 92 extends through the heat exchanger 90 into a logic control unit 96. Logic control unit 96 includes (not shown) an oxygen pressure sensor, a fluid mass flow sensor, a fluid pressure indicator and valve 98 for regulating fluid pressure and flow, a fluid temperature indicator and regulator, a fluid temperature indicator with feedback to a mass sensor, and a timing device for estimating the time fluid in the reservoir 80 will be depleted at the current mass flow. Measurements from this logic control are displayed on an LED digital display 99. Digital display 99 shows the brain resuscitation fluid temperature and flow rate.

Conduit 92 extends from the logic control unit 96, to a terminal point 100 outside the device 70. A high pressure fluid coupling valve 102 is at this terminal point 100. The valve 102 is opened when the device 70 is activated. This terminal point 100 is suitable for attachment of catheter line 104 and subsequent catheters 106.

As with device 20, one way balloon tipped catheters are preferred in alternate device 70. Upon activation the balloon portion of the catheter inflates, blocking possible reverse blood and brain resuscitation solution flow toward the heart. Additionally, it is preferred that device 70 contain openings for venting excess oxygen and for oxygen intake. This oxygen intake can be from the atmosphere or adjunct oxygen sources.

Device 70 is activated when the user pulls the charging handle 86. This action opens a valve 88 on the oxygen tank 82, releasing pressurized oxygen, which moves through channels 85 into the reservoir 80 and into contact with the brain resuscitation solution thereby oxygenating the fluid solution. The pressure from this released oxygen drives the oxygenated solution into conduit 92 which passes through a heat exchanger 90, thereby cooling the solution. Once the cooled oxygenated fluid solution leaves the heat exchanger 90, it continues in conduit 92 through the logic control unit 96.

Once past the logic control unit 96, the solution moves through this conduit 92 until it terminates in a high pressure solution coupling valve 102 outside of the device 70. When the high pressure valve 102 is open, and catheters 106 are coupled to this terminal conduit end 100, brain resuscitation solution can enter the patient's circulatory system. The oxygen pressure preferred is at least 17 psig, sufficient to drive this brain resuscitation solution from the reservoir 80 into the brain.

Other alternative embodiments may have two reservoirs. The first reservoir would be kept at body temperature or slightly cooler whereby this "warm" brain resuscitation solution is available to flood the brain and quickly diffuses in it, whereby the blood-brain barrier is crossed. The second reservoir is available to deliver "cool" (approximately forty degrees fahrenheit) resuscitation solution, chilled by the heat exchanger, for the purpose of inducing hypothermic shock (discussed below).

Still additional alternative embodiments may use preoxygenated solution in the reservoirs. Reservoirs containing preoxygenated fluid solution eliminate the need for oxygen tanks as these devices have sufficient power (enhanced electronics and powerful pumps), capable of moving the brain resuscitation solution from the reservoir in the device to the brain.

While these two preferred embodiments are portable devices particularly suited for portable, field use, they are also suited for stationery, clinical use. Should a clinical device be desired, these two portable embodiments could be made larger and modified accordingly for such use.

In operation, the brain resuscitation device supplies treatment solution for the accompanying resuscitation method. As previously stated, the invention comprises a method of treating anoxic and ischemic injuries suffered as a result of cardiac arrest, suffocation, drowning, electrocution, losses of circulation, strokes, bodily injuries, toxic (carbonmonoxide, cyanide, etc.) poisoning, and associated major trauma.

Reference is now made to FIGS. 4 and 5 which describe and show the non-invasive method of the invention. Preferably, this method involves the initial step of shunting all effective cardiac output away from the lower extremeties and the abdomen 112 and toward the patient's heart and head at step 112. This shunting is preferably accomplished with mast trousers or pneumatic compression suits, which compress the lower abdomen and lower extremities forcing blood to the heart. However, other equivalent devices may be employed. During this time, the patient's lungs are ventilated with 100% oxygen along with basic cardiac life support or chest percussion and ventilation at step 114.

An artificial circulation through the brain is established at step 116 as the patient 118 is catheterized at an injection point along the circulatory system 120. The brain resuscitation solution enters the circulatory system through at least one blood vessel (artery or vein). Preferably, at least one external or internal carotid artery is catherized. These cartoid arteries are preferred since they are large arteries leading directly to the brain and can be easily found by feeling for the carotid pulse. Alternately, any other blood vessel (artery or vein) may be the injection point catherized. Such points include the fermoal arteries, or jugular veins.

Balloon type catheters 121 with one way balloon valves at a distal point are preferred. Once inserted into the arteries, the balloons inflate, limiting any reverse blood and brain resuscitation fluid solution flow toward the heart through the artery.

Prior to catherization, the catheter lines 122 are attached to the brain resuscitation device. This device is now activated and temperature controlled (chilled) oxygenated brain resuscitation solution is delivered to the brain at step 124. This brain resuscitation solution is a mixture of various components suitable for treating these ischemic and anoxic injuries and keeping the brain and associated neurologic tissues intact. Specifically, the brain resuscitation solution is a fluid mixture containing barbituates, oxygen carrying agents, antioxidants, Lazeroids, carrier vehicles, nutrients and other chemicals.

Initially the solution is temperature controlled, and delivered to the brain after having been chilled to approximately forty degrees F. At this temperature, the brain is hypothermically shocked and its metabolism, and subsequent free radical production is slowed. This temperature controlling (cooling) step 124 may alone allow an additional thirty minutes of brain viability. Additional cooling is achieved by applying external cooling means to the patient's head. The cooling means includes bonnets containing ice cubes, synthetic cooling packets and the like. These bonnets may extend to cover the neck and spinal column.

Barbituates comprise from about 0.000 to 20.00 percent by volume of the brain resuscitation solution. Preferably, the brain resuscitation solution includes 0.001 to 10.00 percent by volume of barbituates. These barbituates drive the brain into a submetabolic coma at step 126. Brain metabolism and subsequent free radical production are further lowered.

Thiopental is the preferred barbituate. It has a fast induction time as it can cross the blood-brain barrier in three to seven seconds. Alternately, Secobarbital or Pentobarbital may be used.

Oxygen carrying agents comprise from about 0.00 to 99.90 percent by volume of this brain resuscitation solution. The preferred brain resuscitation solution includes 10.00 to 99.90 percent by volume of oxygen carrying agents. Perfluorocarbons are the preferred oxygen carrying agents, as they have an extremely high oxygen carrying capacity. When delivered to the brain, in this oxidation step 128, these perfluorcarbons are supersaturated with oxygen, having been oxygenated in the fluid reservoir. These perfluorcarbons act as a blood substitute, carrying oxygen to the brain similar to hemoglobin in the blood. These perflurocarbons are temperature controlled and enter the patient's circulation at temperatures between 0 and 105 degrees F.

Antioxidants comprise from about 0.00 to 50.00 percent by volume of this brain resuscitation solution. Preferably, the brain resuscitation solution includes 0.001 to 30.00 percent by volume of antioxidants. These antioxidants are the preferred free radical scavengers. Once introduced into the brain at step 130, these antioxidants compete with brain tissue proteins as binding sites for the free radicals, mainly ionic $O_2^-$. Since a large portion of the free radicals complex with antioxidants, a substantial amount of free radical damage is prevented since these same free radicals do not bind and form complexes with proteins in the brain and associated neurologic tissues. The preferred antioxidants include Vitamin A, Vitamin B, Vitamin C, Vitamin E, Selenium, Cystine, Cysteine, BHT, BHA, Hydergine ® and the like.

Lazaroids, as experimental drug class being developed by the Upjohn Co. of Kalamazoo, Mich., comprise about 0.00 to 30.00 percent by volume of the brain resuscitation solution. Preferably, Lazaroids comprise 0.001 to 20.00 percent by volume of the brain resuscitation solution. These Lazaroids are the preferred agents for protecting and reversing anoxic brain injury for up to forty five minutes of anoxia, as shown in animal studies. These Lazaroids as well as nutrients, are introduced to the brain at step 132 in the brain resuscitation solution. Lazeroids are also free radical scavengers which fall under two major root moieties: pregnanes, ranging in molecular weight from roughly 580-720 and benzopyrans, ranging in molecular weight from 425-905.

The brain resuscitation solution may include up to 50 percent by volume of components which act as carrier vehicles and diluents for the antioxidants, barbituates, perflurocarbons and Lazaroids. Dimethylsulfoxide (DMSO) is the preferred carrier as it aids the above agents in traversing brain cell membranes. Additionally, the brain resuscitation solution may contain physiologic buffers to maintain pH.

Nutrients are also provided in this solution, up to 30 percent by volume. Glucose is one nutrient which is preferred.

Finally, the solution may contain up to 10 percent by volume of heparin or other suitable anti-blood coagulating agents to stop blood clotting which may occur due to lack of blood flow during the resuscitation attempt as a side effect of arterial system blockage and fluid backflow from the balloon tipped catheter.

Once this method has been performed and the brain resuscitation fluid has been properly administered, continuing efforts to restart the heart and restore the circulation at step 134 should be made.

Alternately, a method exists for use in emergency situations. In these situations, preoxygenated fluid may be directly injected into the patient's circulatory system. This is done by removing the reservoir cannister from the brain resuscitation device and attaching it to a catheter line and then catheterizing the patient's circulatory system, or placing fluid from the reservoir cannister into a syringe and injecting the patient.

From the foregoing description, it is clear that those skilled in the art could make changes in the described embodiments and methods of the invention without departing from the broad inventive concepts thereof. It is understood, therefore, that this invention is not limited to the particular embodiment disclosed, but it is intended to cover any modifications which are within the spirit and scope of the claims.

What is claimed is:

1. A method of treating anoxic or ischemic brain and associated nervous tissue injury comprising:
   a. establishing an artificial circulation in a patient's circulatory system by cathertizing said patient at an injection point;
   b. driving the brain into a comatose state by introducing barbiturates through said catheter;
   c. oxygenating the brain by introducing oxygen carrying agents through said catheter;
   d. lowering the brain temperature by introducing cooled fluid through said catheter, said cooled fluid being at a temperature below body temperature;
   e. inhibiting free radical damage by introducing free radical scavengers through said catheter;
   whereby metabolic rates of said tissues are slowed during treatment and said patient remains substantially neurologically intact.

2. The method of claim 1, wherein said method involves the initial step of applying means to said patient for shunting all effective cardiac output away from the lower extremities and lower abdomen to the internal organs including the heart and the brain.

3. The method of claim 1, wherein said method further involves the step of introducing nervous tissue protecting agents and damage reversing agents through said catheter.

4. The method of claim 1, wherein said injection point is at least one blood vessel.

5. The method of claim 4, wherein said blood vessel is at least one carotid artery.

6. The method of claim 5, wherein said artificial circulation establishing step further includes using a balloon catheter with a valve at a distal point on said catheter, and inflating said balloon once said catheter is completely inserted into said external carotid artery to block said external carotid artery, limiting reverse blood flow through said blood vessel toward the heart.

7. The method of claim 1, wherein said oxygen carrying agents include perfluorocarbons.

8. The method of claim 1, wherein said fluid is cooled to approximately 40 degrees Fahrenheit.

9. The method of claim 1, wherein said free radical scavengers include antioxidants.

10. The method of claim 9, wherein said antioxidants comprise: Vitamin A, Vitamin B, Vitamin C, Vitamin E, Selenium, Cystine, Cysteine, BHT, BHA and Hydergine.

11. The method of claim 3, wherein said protecting and reversing agents include Lazaroids.

12. A method of treating anoxic and/or ischemic brain and associated nervous tissue injury comprising:
   a. providing a solution including barbiturates, free radical scavengers and oxygen carrying agents;
   b. oxygenating said solution;
   c. cooling said solution to a temperature substantially below body temperature;
   d. introducing said solution into a patient at an injection point within said patient's body;
   whereby metabolic rates of said nervous tissues are slowed during treatment.

13. The method of claim 12 wherein said method involves the initial step of applying means to said patient for shunting all effective cardiac output away from the lower extremities and lower abdomen to the internal organs including the heart and the brain.

14. The method of claim 12, wherein injection step further includes providing said solution with nervous tissue protecting agents and nervous tissue damage reversing agents.

15. The method of claim 12, wherein said oxygen carrying agents include perfluorocarbons.

16. The method of claim 12, wherein said injection point is at least one blood vessel whereby said solution uses the circulatory system in moving to the brain.

17. The method of claim 12, further including the step of employing a balloon catheter with a distal end valve, said catheter limiting reverse blood flow through the blood vessel toward the heart.

18. The method of claim 12, wherein said free radicals scavengers include the antioxidants: Vitamin A, Vitamin B, Vitamin C, Vitamin E, Selenium, Cystine, Cysteine, BHT, BHA, and Hydergine.

19. The method of claim 12, wherein said solution is cooled to approximately 40 degrees Fahrenheit.

20. The method of claim 14, wherein said nervous tissue protecting agents and said nervous tissue damage reversing agents include Lazaroids.

21. A method of treating anoxic and/or ischemic brain and associated nervous tissue injury comprising:
   a. providing a portable brain resuscitation device including:
      i. at least one fluid reservoir containing brain resuscitation solution;
      ii. oxygenating means in fluid communication with said reservoir;
      iii. means for controlling the temperature of said resuscitation solution, said temperature controlling means being in fluid communication with said reservoir;
      iv. injection means for moving said solution from said device to a patient, said injecting means being removably attached to said portable brain resuscitation device at a point in communication with said temperature adjusting means;

b. cooling said brain resuscitation solution to substantially below body temperature so as to slow the metabolic rate of the brain and associated nervous tissues;

c. injecting said cooled fluid into an injection point along the patient's circulatory system.

22. The method of claim 21, wherein said method involves the initial step of applying means to a patient for shunting all effective cardiac output away from the lower extremities and lower abdomen to the internal organs including the heart and the brain.

23. The method of claim 21, wherein said oxygenating means includes an oxygenator.

24. The method of claim 21, wherein said temperature controlling means includes a heat exchanger.

25. The method of claim 21, wherein said injecting means includes a balloon catheter with a valve at its distal end.

26. The method of claim 21, wherein said injection point is at least one blood vessel.

27. The method of claim 21, wherein said solution is cooled to approximately 40 degrees Fahrenheit, so as to hypothermically shock the brain and associated neurologic tissues.

28. The method of claim 21, wherein said brain resuscitation solution comprises:

a. barbiturates, in an amount effective to induce a coma in the brain and associated nervous tissues, whereby metabolic rates of said tissues are slowed;

b. oxygen carrying agents in an amount effective to transport oxygen to the brain and associated nervous tissues; and c. free radical scavengers, in an amount effective to reverse the oxidative state and inhibit free radical production within said tissues.

29. The method of claim 28 wherein said brain resuscitation fluid additionally comprises an effective amount of nervous tissue protecting and nervous tissue damage reversing agents.

30. The method of claim 28 wherein said oxygen carrying agents include perfluorocarbons.

31. The method of claim 28 wherein said free radicals scavengers include antioxidants.

32. The method of claim 31, wherein said antioxidants comprise: Vitamin A, Vitamin B, Vitamin C, Vitamin E, Selenium, Cystine, Cysteine, BHT, BHA, and Hydergine.

33. The method of claim 29, wherein said nervous tissue protecting and nervous tissue damage reversing agents include Lazaroids.

* * * * *